United States Patent [19]

Ogawa et al.

[11] Patent Number: 4,777,297

[45] Date of Patent: Oct. 11, 1988

[54] PROCESS FOR PREPARING BIS-(4-HYDROXY-3,5-DIBROMOPHENYL)-SULFONE DERIVATIVES

[75] Inventors: Yoshikatsu Ogawa, Takatsuki; Haruhiko Hisada, Yao; Takeshi Kasahara, Sakai; Takayoshi Kojima, Kawachinagano; Fumihiko Kizaki, Kaizuka, all of Japan

[73] Assignee: Marubishi Yuka Kogyo Kabushiki Kaisha, Osaka, Japan

[21] Appl. No.: 844,788

[22] Filed: Mar. 27, 1986

[30] Foreign Application Priority Data

Jul. 9, 1985 [JP] Japan .................. 60-149204

[51] Int. Cl.$^4$ ........................... C07C 147/06
[52] U.S. Cl. ........................... 568/33
[58] Field of Search ............. 568/33, 37, 49, 333, 568/641, 637

[56] References Cited

U.S. PATENT DOCUMENTS

| 4,006,118 | 2/1977 | Ogawa et al. ............ 524/171 |
| 4,613,703 | 9/1986 | Hefner .................. 568/33 |

FOREIGN PATENT DOCUMENTS

| 2905397 | 8/1980 | Fed. Rep. of Germany ...... 568/641 |
| 3036554 | 4/1982 | Fed. Rep. of Germany ...... 568/641 |
| 3120556 | 10/1982 | Fed. Rep. of Germany . |

OTHER PUBLICATIONS

Chemical Abstracts, vol. 98, No. 25, Jun. 20, 1983, p. 532, Abstract No. 215315r, Otsuka.

*Primary Examiner*—Mary E. Ceperley
*Attorney, Agent, or Firm*—Michael N. Meller

[57] ABSTRACT

Bis-(4-hydroxy-3,5-dibromophenyl) sulfone is converted to an allyl ether in the presence of an alkali with allyl chloride in the presence of a bromide and/or an iodide, and/or a substance capable of forming a bromide and/or an iodide by reaction with the alkali.

5 Claims, No Drawings

PROCESS FOR PREPARING BIS-(4-HYDROXY-3,5-DIBROMOPHENYL)-SULFONE DERIVATIVES

BACKGROUND OF THE INVENTION (1) Field of the Invention

The present invention relates to a process for the preparation of bis-(4-hydroxy-3,5-dibromophenyl)-sulfone derivatives. More specifically, the present invention relates to a process for the preparation of bis-(4-allyloxy-3,5-dibromophenyl)-sulfone and bis-(3,5-dibromo-4-dibromopropyloxyphenyl)-sulfone.

(2) Description of the Related Art

It is known that bis-(4-allyloxy-3,5-dibromophenyl)-sulfone is valuable as a flame retardant or an intermediate for the production of a flame retardant. It is taught in Japanese Examined Patent Publications (Kokoku) No. 50-35103 and 50-23639, U.S. Pat. No. 4,006,118, British Pat. No. 1,356,508 and West German Pat. No. 2,236,435 that bis-(3,5-dibromo-4-dibromopropyloxyphenyl)-sulfone obtained by brominating the allyl group of bis-(4-allyloxy-3,5-dibromophenyl)-sulfone according to reaction 3 shown below is very valuable as a flame retardant for polypropylene and the like.

As the conventional process for preparing bis-(4-allyloxy-3,5-dibromophenyl)-sulfone by etherifying bis-(4-hydroxy-3,5-dibromophenyl)-sulfone (hereinafter referred to as "TBS"), there can be mentioned a process in which, as disclosed in the above patent references, TBS is dissolved in methanol, water or the like together with NaOH, allyl bromide is added to the solution, the mixture is heated and refluxed to obtain a viscous resinous precipitate composed mainly of an allyl ether of TBS and the precipitate is washed and purified with methanol or the like (reaction 2). If allyl chloride is used instead of allyl bromide in this reaction 2, the reaction speed of the etherification is very low and bis-(4-allyloxy-3,5-dibromophenyl)-sulfone is hardly formed. The etherification speed in the conventional reaction using allyl bromide is high, but this process is defective in the following points.

(1) Since allyl bromide is readily decomposed by an alkali during the reaction, it is necessary to use allyl bromide and the alkali in excessive amounts. Moreover, it is necessary to add allyl bromide and the alkali during the reaction.

(2) The purity of the product is low, and the product should be purified by methanol washing, alkali washing or the like.

(3) Since the molecular weight of allyl bromide is 121 and the molecular weight of allyl chloride is 76.5, for performing the same etherification, allyl bromide should be used in an amount about 1.6 times the necessary amount of allyl chloride.

(4) Allyl bromide is more expensive than allyl chloride.

(5) The storage stability of allyl bromide is poor and allyl bromide is readily deteriorated. Accordingly, it is necessary to handle allyl bromide very carefully and as-distilled allyl bromide should be used for the reaction.

Reaction 1

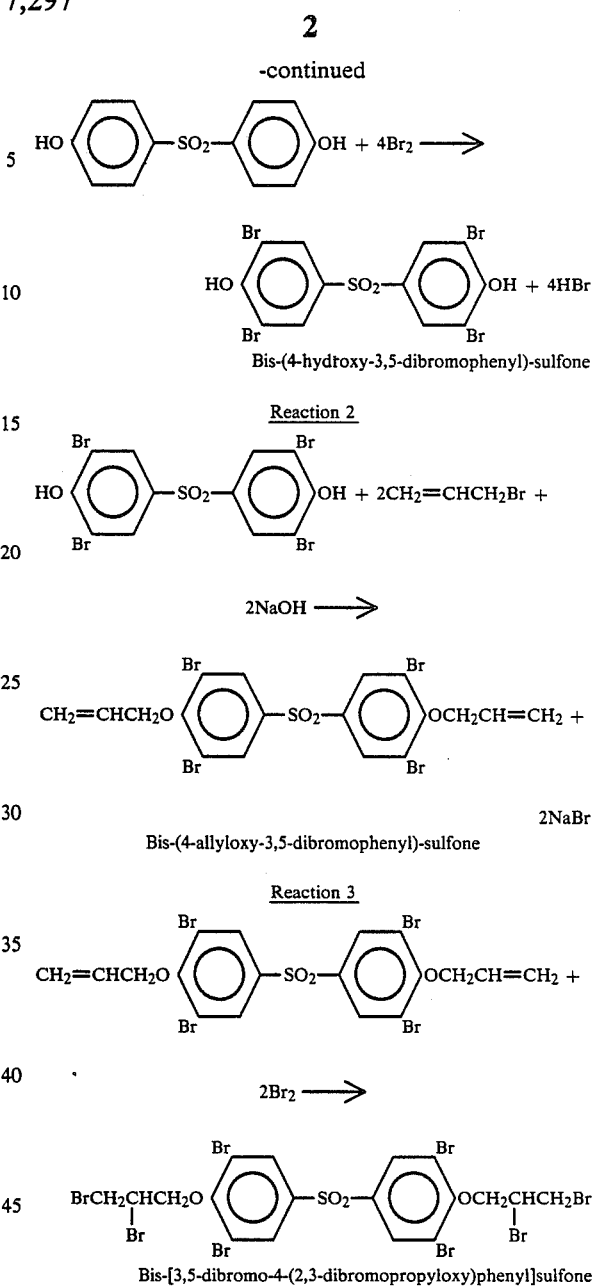

SUMMARY OF THE INVENTION

The present invention is to solve the above-mentioned problem involved in the conventional techniques. Namely, we made research with a view to overcoming the foregoing defects and as the result, we found a process capable of preparing bis-(4-allyloxy-3,5-dibromophenyl)-sulfone and bis-(3,5-dibromo-4-dibromopropyloxyphenyl)-sulfone having a higher purity in a higher yield and at a lower cost by using a less expensive starting material than in the conventional processes. We have now completed the present invention based on this finding.

More specifically, in accordance with the present invention, there is provided a process for the preparation of bis-(4-hydroxy-3,5-dibromophenyl)-sulfone derivatives represented by the following formula:

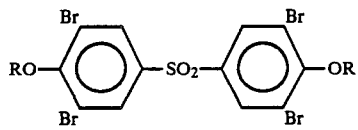

wherein R stands for —CH₂CH=CH₂ or

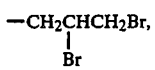

which comprises converting bis-(4-hydroxy-3,5-dibromophenyl)-sulfone to an allyl ether in the presence of an alkali and, if desired, brominating the obtained bis-(4-allyloxy-3,5-dibromophenyl)-sulfone, wherein bis-(4-hydroxy-3,5-dibromophenyl)-sulfone is allyl-etherified with allyl chloride in the presence of a bromide and/or an iodide, and/or a substance capable of forming a bromide and/or an iodide by reaction with said alkali.

DESCRIPTION OF THE PREFERRED EMBODIMENTS

In the process of the present invention, it is preferred that the bromide and/or the iodide be used in an amount of 0.01 to 10 moles per mole of bis-(4-hydroxy-3,5-dibromophenyl)-sulfone or the substance be used in such an amount that the bromide and/or the iodide is formed in an amount of 0.1 to 10 moles per mole of bis-(4-hydroxy-3,5-dibromophenyl)-sulfone by reaction with the alkali.

In the present invention, TBS obtained by brominating bis-(4-hydroxyphenyl)-sulfone (hereinafter referred to as "bisphenol S") according to the above-mentioned reaction 1 may be used as the starting material. This embodiment is very advantageous in that HBr formed as a by-product during the reaction can be utilized for the preparation process of the present invention without separating it from the reaction system. Namely, the bromide obtained by neutralizing HBr formed by reaction 1 with NaOH or the like can be utilized as the bromide in the preparation process of the present invention. Furthermore, TBS can be directly used as the starting material without separation from the reaction system or purification in the process of the present invention.

According to the above embodiment, HBr formed as a by-product can be effectively utilized and separation or purification of TBS is not necessary, and hence, the reaction steps can be simplified and the intended product can be prepared at a low cost.

As the bromide and/or the iodide, and/or the substance capable of forming the bromide and/or the iodide, which is used in the process of the present invention, a bromide compound is ordinarily preferable to an iodine compound because the bromine compound is cheaper and has better storage stability than the iodine compound.

As typical examples of the bromide and iodide that can be used in the present invention, there can be mentioned NaBr, KBr, LiBr, NH₄Br, MgBr₂, CaBr₂, AlBr₃, ZnBr₂, FeBr₃, NaI, KI, LiI, NH₄I, MgI₂, CaI₂, AlI₃, ZnI₂, monoethanol amine hydrobromide, quanidine hydrobromide and guanylurea hydrobromide. These compounds may contain water of crystallization.

In the process of the present invention, it is preferable to use such a bromide or iodide that the hydroxide formed by the reaction of the bromide or iodide with an alkali used for the etherification is water-soluble. In the case where a water-insoluble hydroxide is formed, it is necessary to remove the hydroxide by acid washing or the like.

As typical examples of the substance capable of forming a bromide and/or an iodide by reaction with the alkali, there can be mentioned allyl bromide, allyl iodide, hydrogen bromide, bromine and iodine.

It is preferred that the bromide, the iodide or the substance capable of forming a bromide and/or an iodide be used in an amount of 0.01 to 10 moles, especially 0.1 to 5 moles, per mole of TBS. If the amount of the above compound is smaller than 0.01 mole per mole of TBS, no substantial improvement of the reaction speed or yield can be attained, and if the amount of the above compound is larger than 10 moles per mole of TBS, the reaction speed or yield is not particularly increased but a large amount of a solvent should be used.

As typical examples of the solvent used in the present invention, there can be mentioned water, alcohols such as methanol, ethanol, n-propanol and isopropanol, ketones such as acetone, methylethyl ketone and methylisobutyl ketone, and dioxane, DMA, DMF, methyl cellosolve and ethyl cellosolve. These solvents may be used singly or in the form of mixtures of two or more of them. When bisphenol S is used as the starting material, since a bromination reaction takes place, it is preferred that a solvent hardly reactive with bromine be used and bromination be carried out by using a solvent capable of dissolving HBr formed therein, such as water or a water-methanol mixed solvent, and the reaction be thus conducted or other solvent be added according to need.

The allyl etherification is carried out in the presence of an alkali in an amount of at least 2 moles per mole of TBS. As the alkali, there are used hydroxides and carbonates of alkali metals, and NaOH and KOH are preferred. The alkali reacts with the above-mentioned substances forming a bromide or an iodide, whereby NaBr, KBr, NaI, KI, NaOBr, or the like is formed.

The present invention will now be further illustrated with reference to the following non-limitative examples.

EXAMPLE 1

A four-neck flask equipped with a thermometer, a reflux cooler and a stirrer was charged with 900 g of water, and 84 g of NaOH was dissolved therein. Then, 200 g of isopropyl alcohol was added to the solution and 566 g (1 mole) of bis-(4-hydroxy-3,5-dibromophenyl)-sulfone (having a melting point of 289° to 290° C.) was further incorporated and dissolved. Then, 103 g (1 mole) of sodium bromide was incorporated and dissolved in the solution and 191 g (2.5 moles) of allyl chloride was added to the solution, and the mixture was heated and refluxed. Advance of the reaction was checked by sampling a small amount of the reaction liquid and adding HCl thereto to effect acidification, and when the liquid did not show a turbid white or milky white color, it was judged that the reaction was completed. Incidentally, the unreacted compound is dissolved in the alkali and when the reaction liquid is acidified, the reaction liquid becomes turbidly white or milky white if the unreacted substance is present.

The reaction was conducted for 8 hours until the reaction liquid did not show a turbid white or milky white color when a small amount of the reaction liquid waas sampled and acidified by HCl. A white needle crystal of bis-(4-allyloxy-3,5-dibromophenyl)-sulfone was obtained. The crystal was recovered by filtration, washed with water and dried at 80° C. under reduced pressure (15 mmHg). The obtained results are as follows.

Amount formed: 635 g (theoretical amount=646 g).
Yield: 98.2%.
Melting point: 185° to 186° C.
Elementary analysis values:

| Found | Calculated |
| --- | --- |
| C = 33.4% | C = 33.46% |
| H = 2.1% | H = 2.18% |
| O = 9.9% | O = 9.90% |
| Br = 49.4% | Br = 49.48% |
| S = 4.9% | S = 4.96% |

EXAMPLE 2

A four-neck flask equipped with a thermometer, a reflux cooler and a stirrer was charged with 800 g of methyl alcohol and 400 g of water, and 250 g (1 mole) of bisphenol A was dissolved and reacted with 640 g of bromine at a temperature lower than 40° C. to form TBS and HBr. Then, a solution of 252 g (6.3 moles) of NaOH in water was added to the reaction mixture to neutralize HBr and dissolve TBS. Then, 191 g (2.5 moles) of allyl chloride was added to the mixture, and the mixture was heated and refluxed.

The reaction was thus conducted for 8 hours until the reaction mixture did not show a milky white color when a small amount of the reaction liquid was sampled and acidified by HCl. A white needle crystal of bis-(4-allyloxy-3,5-dibromophenyl)-sulfone was formed. The crystal was recovered by filtration, washed with water and dried at 80° C. under reduced pressure (15 mmHg). The obtained results are as follows:

Amount formed: 631 g (theoretical amount=646 g).
Yield: 97.6%.
Melting point: 185° to 186° C.
Elementary analysis values: C=33.5%, H=2.1%, O=9.9%, Br=49.3%, S=4.9%

EXAMPLE 3

A four-neck flask equipped with a thermometer, a reflux cooler and a stirrer was charged with 900 g of water, and 82 g of NaOH was dissolved therein. Then, 200 g of isopropyl alcohol was added to the solution and 566 g (1 mole) of TBS was further incorporated and dissolved. Then, 30 g (0.247 mole) of allyl bromide and 176 g (2.3 moles) of allyl chloride were added to the mixture, and the mixture was heated and refluxed.

The reaction was thus conducted for 10 hours until the reaction liquid did not show a milky white color when a small amount of the reaction liquid was sampled and acidified by HCl. A white needle crystal of bis-(4-allyloxy-3,5-dibromophenyl)-sulfone was formed. The crystal was recovered by filtration, washed with water, washed with methanol and dried at 80° C. under reduced pressure (15 mmHg). The obtained results are as follows.

Amount formed: 623 g.
Yield: 96.4%.
Melting point: 184.5° to 185.5° C.

Elementary analyis values: C=33.4%, H=2.1%, O=9.9%, Br=49.4%, S=4.9%.

EXAMPLE 4 AND COMPARATIVE EXAMPLE

A four-neck flask equipped with a thermometer, a reflux cooler and a stirrer was charged with 900 g of water, and an alkali in an amount shown below was dissolved and 200 g of isopropyl alcohol was added. Then, 566 g (1 mole) of TBS (having a melting point of 289° to 290° C.) was incorporated and dissolved in the solution. Then, a bromide or iodide shown below was further dissolved and 191 g (2.5 moles) of allyl chloride was added, and reaction was carried out under heat and reflux for a time shown below. Other operations were the same as described in Example 1. When the bromide was MgBr2 or CaBr2, the formed hydroxide was removed by washing with a dilute aqueous solution of hydrochloric acid to effect purification.

For comparison, the reaction was carried out without addition of the bromide or iodide. In this case, even if the reaction was conducted for a long time, the reaction liquid became turbidly white on acidification. Thus, it was confirmed that the reaction speed was very low.

TABLE

| Bromide or Iodide | | Alkali | | Reaction | |
| --- | --- | --- | --- | --- | --- |
| Compound | Amount (moles) | Compound | Amount (moles) | Time (hours) | Yield (%) |
| NaBr | 0.1 | NaOH | 2.1 | 15 | 96.1 |
| NaBr | 1 | KOH | 2.1 | 8 | 97.5 |
| NaBr | 3 | KOH | 2.1 | 8 | 97.6 |
| NaBr | 6 | NaOH | 2.1 | 8 | 98.0 |
| KBr | 0.1 | KOH | 2.1 | 15 | 96.5 |
| KBr | 1 | NaOH | 2.1 | 8 | 98.0 |
| KBr | 4 | NaOH | 2.1 | 8 | 98.0 |
| NaI | 0.1 | NaOH | 2.1 | 15 | 96.2 |
| NaI | 1 | KOH | 2.1 | 8 | 97.8 |
| NaI | 3 | NaOH | 2.1 | 8 | 98.0 |
| KI | 0.1 | NaOH | 2.1 | 15 | 96.0 |
| KI | 1 | KOH | 2.1 | 8 | 97.5 |
| KI | 3 | NaOH | 2.1 | 8 | 97.6 |
| NH4Br | 1 | NaOH | 2.1 | 10 | 96.5 |
| NH4I | 1 | NaOH | 2.1 | 10 | 96.8 |
| LiBr | 1 | KOH | 2.1 | 10 | 97.0 |
| MgBr2 | 0.2 | NaOH | 2.5 | 12 | 95.6 |
| CaBr2 | 0.2 | KOH | 2.5 | 12 | 96.0 |
| Comparative Example | | | | | |
| 1 not added | | NaOH | 2.1 | 15 | 12.5 |
| 2 not added | | NaOH | 2.1 | 30 | 14.5 |
| 3 not added | | KOH | 2.1 | 15 | 13.5 |
| 4 not added | | KOH | 2.1 | 30 | 15.0 |

EXAMPLE 5

In 950 g of methylene chloride was dissolved 323 g (0.5 mole) of bis-(4-allyloxy-3,5-dibromophenyl)-sulfone obtained in Example 2, and 162 g (1.01 moles) of bromine was added to the solution at 30° to 40° C. to effect reaction. The reaction mixture was washed with water, washed with a 0.5% aqueous solution of sodium bicarbonate and washed with water, and methylene chloride was removed by evaporation. Finally, the residue was treated at an inner temperature of 105° C. under reduced pressure (3 mmHg). Thus, 483 g of colorless, transparent and glassy bis-(3,5-dibromo-4-dibromopropyloxyphenyl)-sulfone was obtained. The obtained results are as follows.

Softening point: 50° to 53° C.
Elementary analysis values:

| Found | Calculated |
| --- | --- |
| C = 22.3% | C = 22.38% |
| H = 1.4% | H = 1.46% |
| O = 6.6% | O = 6.62% |
| Br = 66.2% | Br = 66.20% |
| S = 3.3% | S = 3.32% |

Although the obtained bis-(3,5-dibromo-4-dibromopropyloxyphenyl)-sulfone showed a melting point of 50° to 53° C., this was due to the fact that the obtained compound was not crystallized. When the obtained compound was crystallized according to the customary method using an appropriate solvent such as ethylene glycol monomethyl ether (namely, the obtained compound was dissolved in the solvent under heating and the solution was cooled to precipitate a crystal), or when a solution of the obtained compound, for example, a methylene chloride solution, was added to a solvent incapable of dissolving the compound therein, for example, methyl alcohol, to effect crystallization, a crystal having a melting point of 125° C. was obtained. However, when the crystal was heated at a temperature higher than the melting point, the crystal structure was destroyed and an amorphous substance having a softening point of 50° to 53° C. was formed.

We claim:

1. In a process for the preparation of bis-(4-allyloxy-3,5-dibromophenyl)sulfone which comprises converting bis-(4-hydroxy-3,5-dibromophenyl)sulfone to an allyl ether in the presence of an alkali, the improvement which comprises allyl-etherifying bis(4-hydroxy-3,5-dibromophenyl)sulfone with allyl chloride in the presence of a halide selected from the group consisting of NaBr, KBr, LiBr, $NH_4Br$, $MgBr_2$, $CaBr_2$, $AlBr_3$, $ZnBr_2$, $FeBr_3$, monoethanolamine hydrobromide, guanidine hydrobromide, guanylurea hydrobromide, NaI, KI, LiI, $NH_4I$, $ZnI_2$, $MgI_2$, $CaI_2$, $AlI_3$, and substances which form a bromide or an iodide by reaction with said alkali.

2. A process according to claim 1 wherein said substance is used in such an amount that the bromide or iodide is formed in an amount of 0.01 to 10 moles per mole of bis-(4-hydroxy-3,5-dibromophenyl)sulfone by reaction with said alkali.

3. A process according to claim 1, wherein the halide is used in an amount of 0.01 to 10 moles per mole of bis-(4-hydroxy-3,5-dibromophenyl)-sulfone.

4. A process according to claim 1, wherein the substance which forms a bromide by reaction with the alkali is selected from the group consisting of allyl bromide and bromine.

5. A process according to claim 1, wherein the substance which forms an iodide by reaction with the alkali is selected from the group consisting of allyl iodide and iodine.

* * * * *